(12) United States Patent
Jacquin et al.

(10) Patent No.: US 10,829,463 B2
(45) Date of Patent: Nov. 10, 2020

(54) PROCESS FOR SEPARATING FURANIC COMPOUNDS, IN PARTICULAR 5-HYDROXYMETHYLFURFURAL, FROM DIMETHOXYSULFOXIDE BY LIQUID-LIQUID EXTRACTIONS

(71) Applicant: IFP ENERGIES NOUVELLES, Rueil-Malmaison (FR)

(72) Inventors: Marc Jacquin, Lyons (FR); Sophie Drozdz, Brindas (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 16/647,953

(22) PCT Filed: Sep. 10, 2018

(86) PCT No.: PCT/EP2018/074276
§ 371 (c)(1),
(2) Date: Mar. 17, 2020

(87) PCT Pub. No.: WO2019/052937
PCT Pub. Date: Mar. 21, 2019

(65) Prior Publication Data
US 2020/0262803 A1 Aug. 20, 2020

(30) Foreign Application Priority Data

Sep. 18, 2017 (FR) .................................. 17 58605

(51) Int. Cl.
C07D 307/48 (2006.01)
B01D 11/04 (2006.01)
(52) U.S. Cl.
CPC ........ *C07D 307/48* (2013.01); *B01D 11/0488* (2013.01)
(58) Field of Classification Search
CPC .......................... C07D 307/48; B01D 11/0488
See application file for complete search history.

(56) References Cited

U.S. PATENT DOCUMENTS

| | | | |
|---|---|---|---|
| 7,880,049 B2 | 2/2011 | Dumesic et al. | |
| 2004/0222153 A1 | 11/2004 | Baniel et al. | |
| 2009/0124839 A1 | 5/2009 | Dumesic et al. | |
| 2015/0031904 A1* | 1/2015 | Cho | C07D 307/50 549/489 |

FOREIGN PATENT DOCUMENTS

| | | |
|---|---|---|
| FR | 2669635 A1 | 5/1992 |
| FR | 2669636 A1 | 5/1992 |
| WO | 2008/151178 A1 | 12/2008 |

OTHER PUBLICATIONS

International Search Report dated Oct. 11, 2018 issued in corresponding PCT/EP2018/074276 application (2 pages).

* cited by examiner

*Primary Examiner* — Timothy R Rozof
(74) *Attorney, Agent, or Firm* — Millen, White, Zelano and Branigan, P.C.

(57) ABSTRACT

The invention relates to a process for separating furanic compounds from a feedstock additionally containing dimethoxysulfoxide (DMSO). These furanic compounds are in particular 5-hydroxymethylfurfural (5-HMF), 2,5-diformylfuran (DFF), 2,5-furanedicarboxylic acid (FDCA) or dimethyl 2,5-furandicarboxylate (DMFDCA). The process successively comprises a) bringing the feedstock into contact with water originating from step c), then b) a liquid-liquid extraction with an organic solvent followed by a back extraction c) by the water added in order to obtain an organic extract rich in furanic compounds. The extract may then be subjected to a crystallization step d) and then a filtration in order to obtain the solid furanic compound. The water-rich or solvent-rich effluents are advantageously recycled respectively to the back extraction and the extraction.

19 Claims, 2 Drawing Sheets

PROCESS FOR SEPARATING FURANIC COMPOUNDS, IN PARTICULAR 5-HYDROXYMETHYLFURFURAL, FROM DIMETHOXYSULFOXIDE BY LIQUID-LIQUID EXTRACTIONS

TECHNICAL FIELD

The invention relates to a process for the separation of furan compounds, in particular 5-hydroxymethylfurfural (5-HMF), 2,5-diformylfuran (DFF), 2,5-furandicarboxylic acid (FDCA) or dimethyl 2,5-furandicarboxylate (DMFDCA), alone or as a mixture, contained in a feedstock also comprising dimethoxysulfoxide (DMSO), the process being carried out by liquid-liquid extraction.

PRIOR ART

5-HMF, DFF, FDCA or DMFDCA are advantageous compounds resulting from biomass which can be made economic use of in numerous fields, in particular in pharmaceuticals, in agrochemistry or in speciality chemistry. In particular, 2,5-furandicarboxylic acid and dimethyl 2,5-furandicarboxylate are substitutes for terephthalic acid and dimethyl terephthalate respectively as monomer for the production of commodity fiber or plastic.

The production of 5-HMF by dehydration of sugars has been known for many years and has formed the subject of a large number of research studies. There are numerous dehydration conditions, and mention may in particular be made, by way of example, of the following methods:

- 5-HMF can be obtained in an aqueous medium, generally in the presence of an acid catalyst. This acid catalyst makes it possible to dehydrate the C6 sugar (in particular fructose) to give 5-HMF, but also catalyzes the rehydration of 5-HMF to give formic acid and levulinic acid, which is very harmful to the yield.
- 5-HMF can also be obtained in a polar protic medium, with solvents such as methanol, ethanol or acetic acid, and in the presence of an acid catalyst. Under these conditions, 5-HMF is obtained as a mixture with an ether or ester derivative of 5-HMF, depending on the reaction medium used. The formation of these byproducts is due to the reaction of 5-HMF with the reaction solvent in an acid medium.

Application WO 2007/104514 describes the synthesis of 5-HMF by dehydration of sugar using methanol or ethanol as solvent in the presence of an acid catalyst. In this case, the presence of said catalyst also catalyzes the etherification reaction of 5-HMF with the alcohol to give a mixture of 5-HMF and of its methyl or ethyl ether form, depending on the alcohol used as solvent.

- 5-HMF can also be produced in a polar aprotic medium, with or without an acid catalyst. Mention may more particularly be made of the use of dimethyl sulfoxide (DMSO) which, with or without an acid catalyst, makes it possible to produce 5-HMF with very good yields, and without the undesirable reactions listed above.

Furthermore, whatever the synthesis medium (water, methanol, DMSO, and the like), polymeric byproducts called humins are formed during the production of 5-HMF (van Dam, H. E.; Kieboom, A. P. G.; van Bekkum, H. (1986), The Conversion of Fructose and Glucose in Acidic Media: Formation of Hydroxymethylfurfural, in: Starch—Stärke, Vol. 38, No. 3, pp. 95-101).

The synthesis of 5-HMF in a medium such as DMSO is particularly advantageous, as it makes it possible to obtain 5-HMF in its alcohol form with very good yields. Nevertheless, the physicochemical properties of DMSO make it very difficult to separate from 5-HMF by the usual methods known to a person skilled in the art.

By way of illustration, the methods for distillation of the reaction medium can be suitable for removing the water present in the reaction medium. On the other hand, distillation does not make it possible to treat the heavy fraction containing mainly DMSO, 5-HMF and humins. This is because, as 5-HMF and the humins are less volatile than DMSO, they become concentrated at the bottom of the distillation column. Under the effect of the temperature and of the increase in the concentration, 5-HMF undergoes degradation reactions, in particular condensation and polymerization, which induce a strong fall in the yield of 5-HMF. Besides the loss of yield of 5-HMF, a strong coloring of the 5-HMF from yellow to black is observed, which can be problematic for its subsequent use. For all these reasons, distillation is thus not a suitable method, in particular with a view to industrial operation.

Furthermore, the crystallization of 5-HMF from DMSO cannot be envisioned for an industrial application. These two compounds form a deep eutectic for a median composition which prevents the recovery of one or the other of the pure compounds with good yields.

To date, the only industrializable alternative for the extraction of 5-HMF from a reaction medium containing DMSO is liquid-liquid extraction, followed by a crystallization of the extract, as described in the patent FR 2 669 635.

According to this patent, in a first stage, water is added to the reaction medium in order to be able to carry out a liquid-liquid extraction with a water-immiscible solvent, such as dichloromethane or else diethyl ether. This separation technique is effective from a point of view of the yield (91-98%) [as shown by the c9 values in examples 1 to 5 of this patent] but the extract recovered is impure. In particular, the extract contains a not insignificant amount of DMSO [c10 values in examples 1 to 5].

Thus, the purity of the 5-HMF recovered in the extract (excluding extraction solvent) is less than 90-93% in examples 1 to 5 of the patent FR-2 669 635: the purity being defined as the amount of 5-HMF/amount of DMSO+amount of 5-HMF ratio, i.e. the c8/(c8+c10)*100 ratio.

In a second stage, a part of the extraction solvent (dichloromethane or diethyl ether) is evaporated so as to produce a solution more concentrated in 5-HMF (and in DMSO jointly extracted with the 5-HMF) in the extraction solvent; then this more concentrated solution is cooled with the aim of crystallizing the 5-HMF, which is recovered by filtration. The crystallization yield is typically of the order of 69-72% [e5 values of the examples]. This operation is thus repeated on the filtrate with the aim of obtaining an overall crystallization yield of the order of 90-94% [e7 values of examples 1 to 5].

The process proposed in this patent FR 2 669 635 thus makes it possible to obtain a good overall extraction yield of 5-HMF by carrying out a liquid-liquid extraction, followed by a crystallization of the extract.

Nevertheless, we have found that the presence of DMSO (jointly extracted with the 5-HMF) in the crystallization stage is detrimental.

This is because the presence of DMSO greatly increases the solubility limit of 5-HMF, and induces a delay in the nucleation and growth of the 5-HMF crystals. The increase in the solubility limit has a negative impact on the operating costs of the process as, in order to obtain one and the same crystallization yield in the presence of DMSO, it is necessary to cool the medium further. Furthermore, the delay in the nucleation and in the growth of the 5-HMF crystals has a negative impact on the capital costs of the process as, in order to obtain one and the same crystallization yield in the presence of DMSO, it is necessary to generate more residence time, and thus to use bulkier crystallizers.

Furthermore, 2,5-diformylfuran (DFF) and 2,5-furandicarboxylic acid (FDCA) can be obtained by oxidation of 5-HMF in DMSO. Furthermore, dimethyl 2,5-furandicarboxylate (DMFDCA) can be obtained by esterification of 2,5-furandicarboxylic acid (FDCA), still in DMSO, in the presence of methanol. These compounds have physicochemical properties which are relatively close to those of 5-HMF, and the problem set out above can be generalized from 5-HMF to these other furan compounds.

The applicant company proposes an improvement to the process described in the patent FR 2 669 635. This improvement is based on the modification of the extraction stage, in particular by adding a stage of back-extraction with water.

The purity of the 5-HMF extracted is thus improved, for one and the same amount of water added. A purity of 95% or more, indeed even of at least 98%, can be obtained. In particular, this back-extraction reduces the amount of DMSO contained in the extract.

The stage of crystallization of the 5-HMF from the purified extract can be carried out under much more favorable conditions. In particular, the crystallization of the 5-HMF from the purified extract can be carried out at higher temperatures (thus limiting the energy consumption) and lower crystallizer volumes (thus limiting the capital costs).

The crystallization of this purified extract (i.e. devoid of DMSO) makes it possible to obtain a better crystallization yield of the 5-HMF, all things otherwise being equal, and thus to obtain a filtrate containing less 5-HMF. The recycling of this filtrate containing less 5-HMF as extraction solvent, then makes it possible to obtain a better extraction yield in an industrial process operating continuously. The addition of this stage of back-extraction with water thus makes possible an improved operation of the process, described in the patent FR 2 669 635, of extraction of the 5-HMF and crystallization of the 5-HMF from the extraction solvent.

OBJECT OF THE INVENTION

An object of the present invention is thus to provide a process for the separation of furan compounds and more particularly of 5-HMF, from a feedstock comprising at least DMSO, by liquid-liquid extraction.

Another object of the invention is to provide a process for the separation of furan compounds and more particularly of 5-HMF crystallized under mild conditions.

BRIEF DESCRIPTION OF THE INVENTION

The invention relates to a process for the separation of the furan compound(s) contained in a feedstock also comprising dimethoxysulfoxide (DMSO), said process successively comprising the following stages:
a) a stage a) in which said feedstock is brought into contact with the intermediate aqueous raffinate enriched in DMSO produced in stage c) and the mixture is optionally filtered,
b) a stage b) of extraction of said mixture produced in stage a) by an organic solvent chosen from chlorinated solvents, ethers, ketones and aromatic compounds, producing an aqueous raffinate enriched in DMSO and an intermediate organic extract enriched in furan compound(s),
c) a stage c) of back-extraction of said intermediate organic extract enriched in furan compound(s) produced in stage b) by water added, producing an intermediate aqueous raffinate enriched in DMSO and a purified organic extract, and said intermediate aqueous raffinate is introduced, partially or completely, in stage a).

The purity of the furan compound (in particular 5-HMF) in the purified organic extract produced in stage c) is at least 93%, and generally at least 95%, calculated as being the ratio of the amount of furan compounds/amount of furan compounds+amount of DMSO in this purified organic extract.

Preferably, the process additionally comprises a stage d) of crystallization of the furan compound(s) contained in said purified extract produced in stage c), followed by a filtration, and there is obtained said solid compound, on the one hand, and a filtrate rich in solvent, on the other hand. Rich in solvent is understood to mean more than 80% by weight of solvent, preferably more than 90% by weight of solvent. The filtrate resulting from stage d) is then cleverly recycled, partially or completely, to stage b) as organic solvent in order to carry out the extraction stage. A new extraction of said furan compound (and in particular of 5-HMF) can then be carried out.

In a preferred embodiment of the invention, the aqueous raffinate enriched in DMSO produced in stage b) is distilled, preferably under vacuum. A residue rich in DMSO, on the one hand, and a distillate rich in water, on the other hand, are obtained. Rich is understood here to mean more than 95% by weight, preferably more than 98% by weight.

A part or all of the distillate rich in water can be cleverly recycled in stage c) as water added in order to carry out the back-extraction stage. The residue rich in DMSO can cleverly be reused in the upstream synthesis process in order to produce more furan compound (for example 5-HMF).

Generally, the amount of water in the mixture produced in stage a) is from 10% to 90% by weight. This amount of water is dependent on the organic solvent introduced in stage b).

The solvent of stage b) is preferably chosen from the group formed by $C_1$-$C_{10}$ chlorinated solvents, $C_2$-$C_{10}$ ethers, $C_2$-$C_{10}$ ketones and $C_4$-$C_{10}$ aromatic compounds.

Generally, stages b) and c) take place at a temperature of 0 to 60° C., preferably of 10 to 30° C., preferably at ambient temperature.

Preferably, the back-extraction water added in stage c) contains less than 1% by weight of DMSO, preferably less than 0.1% by weight of DMSO.

The furan compound is preferably chosen from the group formed by 5-hydroxymethylfurfural (5-HMF), 2,5-diformylfuran (DFF), 2,5-furandicarboxylic acid (FDCA) and dimethyl 2,5-furandicarboxylate (DMFDCA), alone or as a mixture.

The invention particularly relates to a process in which the furan compound is 5-hydroxymethylfurfural (5-HMF).

Thus, the invention relates in particular to a process for the extraction of 5-HMF by liquid-liquid extraction from a feedstock comprising 5-HMF and DMSO, said process successively comprising the stages:
a) a stage a) in which said feedstock is brought into contact with the intermediate aqueous raffinate enriched in DMSO produced in stage c) and the mixture is optionally filtered, b) a stage b) of extraction of the mixture produced in stage a) by an organic solvent chosen from chlorinated solvents, ethers, ketones and aromatic compounds, producing an aqueous raffinate enriched in DMSO and an intermediate organic extract enriched in 5-HMF; optionally, said aqueous raffinate is distilled, and a residue rich in DMSO, on the one hand, and a distillate rich in water, on the other hand, are obtained, c) a stage c) of back-extraction of the intermediate organic extract enriched in 5-HMF produced in stage b) by water added, producing an intermediate aqueous raffinate enriched in DMSO comprising at least 60% by weight of water and a purified organic extract, and said intermediate aqueous raffinate is recycled, partially or completely, to stage a), d) optionally, a stage of crystallization of the 5-HMF contained in the purified organic extract produced in stage c), followed by a filtration, and solid 5-HMF and a filtrate rich in solvent are obtained.

DETAILED DESCRIPTION OF THE INVENTION

It will most often be done in connection with 5-HMF but it can be extended to the other furan compounds mentioned.

The Feedstock Entering in Stage a)

In accordance with the present invention, the feedstock of the separation process contains at least one furan compound and DMSO. Mention may be made, among the furan compounds, of 5-hydroxymethylfurfural (5-HMF), 2,5-diformylfuran (DFF), 2,5-furandicarboxylic acid (FDCA) and dimethyl 2,5-furandicarboxylate (DMFDCA), alone or as a mixture.

The invention applies in particular to a feedstock containing 5-HMF.

It results from the processes for the manufacture of 5-HMF by dehydration of sugars in a reaction medium comprising DMSO; these processes are well known to a person skilled in the art.

Sugar is understood to mean glucose or fructose, alone or as a mixture, sucrose, but also oligosaccharides, such as cellobiose, cellulose or indeed even inulin. Sugar is thus generally understood to mean a sugar containing 6 carbon atoms (hexoses) but this does not exclude the presence in the feedstock of sugars containing 5 carbon atoms (pentoses).

The DMSO generally represents more than 40% by weight of the feedstock of the separation process, indeed even more than 60% by weight of the feedstock of the separation process.

The furan compound(s) represent more than 1% by weight of the feedstock of the separation process, preferably more than 10% by weight, preferably more than 20% by weight.

Furthermore, this feedstock can contain water even before it is mixed with the intermediate aqueous raffinate in stage a). This water may have been formed by the dehydration reaction of the sugar to give 5-HMF (3 moles of water per mole of 5-HMF), or also by the esterification reaction of FDCA to give DMFDCA (2 moles of water per mole of FDCA). Likewise, this water may also have been introduced with the sugar, in the case where, for practical reasons, a syrup of sugar at approximately 70% by weight in water had been used.

Thus, the feedstock can contain water, in a proportion generally of between 0.1% and 30% by weight, preferably between 0.1% and 15% by weight.

The Organic Extraction Solvent Entering Stage b)

In accordance with the invention, the organic extraction solvent introduced in stage b) is chosen from water-immiscible solvents, so as to form two liquid phases in the back-extraction stage c), but also in stage b) of extraction in the presence of a high proportion of DMSO in the raffinate. This property is highly dependent on the relative proportion of the flow rates of feedstock, of back-extraction water and of extraction solvent employed in the process.

Without limitation, the solvent is chosen from the family of chlorinated solvents, ethers, ketones and aromatic compounds. Preferably, these are $C_1$-$C_{10}$ chlorinated solvents, $C_2$-$C_{20}$ ethers, $C_2$-$C_{10}$ ketones or $C_4$-$C_{10}$ aromatic compounds. Preferably, the solvent is chosen from dichloromethane, diethyl ether, diisopropyl ether, methyl ethyl ketone, methyl isopropyl ketone, thiophene, anisole and toluene. Very preferably, the solvent is dichloromethane.

Preferably, the solvent is pure (at least of commercial purity).

It should be noted that, in the preferred embodiment of the invention where the filtrate rich in organic solvent obtained in stage d) is recycled in stage b), the latter can contain a residual amount of furan compound and of DMSO.

The residual amount of DMSO will be lower the more efficiently the back-extraction has been carried out in stage c).

The residual amount of furan compound will be lower the more efficiently the crystallization has been carried out in stage d).

The Back-Extraction Water Added in Stage c)

Back-extraction water added in stage c) is understood to mean a flow which contains more than 95% by weight of water, preferably more than 98% by weight of water.

It should be noted that, in the preferred embodiment of the invention where the aqueous raffinate enriched in DMSO produced in stage b) is distilled, and where the distillate rich in water thus obtained is used to feed stage c), the latter can still contain a residual amount of DMSO.

The residual amount of DMSO will be smaller the more efficiently the distillation has been carried out in stage b).

The efficiency of the backwashing will be greater the lower the amount of DMSO present in the back-extraction water added. Preferably, the back-extraction water added thus contains less than 1% by weight of DMSO, preferably less than 0.1% by weight of DMSO.

The Mixing Stage a)

According to the invention, said feedstock containing at least one furan compound and DMSO is mixed with the intermediate aqueous raffinate enriched in DMSO resulting from the back-extraction stage c), which intermediate aqueous raffinate is introduced partially or completely in stage a). This intermediate aqueous raffinate contains more than 60% by weight of water, preferably more than 80% by weight of water.

The resulting mixture contains from 10% to 90% by weight of water, preferably 20-80% by weight of water.

By increasing the water content, some of the possible "humin" byproducts precipitate. "Humins" refers to all the undesirable polymeric compounds formed during the synthesis of 5-HMF. The humins can represent up to 30% by weight of the feedstock and often are of the order of 20% by weight. They can be quantified in various ways well known to a person skilled in the art, such as, for example, by size exclusion chromatography. An optional filtration operation thus makes it possible to remove the "humins" which have precipitated. The filtrate obtained is then sent to the liquid-liquid extraction stage b). When the amount of humins in the feedstock is low (for example, 1% by weight or less), it is possible to dispense with the filtration stage a).

Stage a) generally takes place at a temperature of 0 to 60° C., preferably from 10 to 30° C. and generally at ambient temperature.

The Extraction Stage b)

The liquid-liquid extraction carried out in stage b) is an extraction of the mixture obtained in stage a) countercurrentwise to the organic solvent. This technique is well known to a person skilled in the art. The extraction can be carried out, for example, in a mixer-settler array, in a column filled with random or structured packing, in a plug-flow column, or indeed even in a stirred column.

The extraction is generally carried out at a temperature of between 0 and 60° C., preferably between 10 and 30° C., i.e. most often at ambient temperature.

The proportion (w/w) of solvent is preferably from 0.2 to 5, with respect to the mixture introduced; the ratio can be greater (for example up to 70) in stirred columns.

On the one hand, a flow depleted in furan compound, known as aqueous raffinate, which contains a large part of the DMSO initially contained in the feedstock, and, on the other hand, a flow enriched in furan compound, known as intermediate organic extract, which contains a large part of the furan compound(s) initially contained in the feedstock, are recovered. This intermediate extract also contains a small amount of DMSO.

The intermediate organic extract enriched in 5-HMF is directed to the back-extraction stage c).

The aqueous raffinate can undergo various treatments in order to separate the water from the DMSO, which predominantly constitute it. Thus, in a preferred embodiment of the invention, the aqueous raffinate is distilled under vacuum in order to recover a residue rich in DMSO, on the one hand, and a distillate rich in water, on the other.

This residue rich in DMSO can advantageously be sent to a unit for the synthesis of 5-HMF (for example by dehydration of sugars).

The distillate rich in water can, completely or partially, be advantageously recycled in stage c) as water added.

Stage c)

According to the invention, the intermediate organic extract enriched in 5-HMF obtained in stage b) is subjected to a stage of back-extraction by water added.

The introduction of water is carried out so as to implement the extraction, according to the general knowledge of a person skilled in the art. It is quite certain that the addition of water is as low as possible so as to reduce the costs, but sufficient to guarantee a purity of the furan compound of at least 93%, preferably of at least 95%. The amount of water added is such that the amount of water in the mixture of stage a) is between 10-90% by weight of the feedstock, often between 20-80%.

The liquid-liquid extraction carried out in stage c) is an extraction of the intermediate organic extract obtained in stage b) countercurrentwise to the water added. This technique is well known to a person skilled in the art. The extraction can be carried out, for example, in a mixer-settler array, in a column filled with random or structured packing, in a plug-flow column, or indeed even in a stirred column.

The extraction is generally carried out at a temperature of between 0 and 60° C., preferably between 10 and 30° C., i.e. most often at ambient temperature.

The proportion (w/w) of solvent is preferably from 0.2 to 5, with respect to the mixture introduced; the ratio can be greater (for example up to 70) in stirred columns.

An aqueous flow enriched in DMSO, known as intermediate aqueous raffinate, generally containing at least 60% by weight of water, preferably at least 80% by weight of water, and a purified organic extract are recovered. This intermediate aqueous raffinate is preferably introduced, partially or preferably completely, in stage a).

The furan compound or more particularly the 5-HMF contained in the extract obtained exhibits a purity of greater than 93% by weight, and generally of 95% or more, indeed even of at least 98% (amount of 5-HMF/amount of 5-HMF+ amount of DMSO).

At the same time, the amount of DMSO contained in the organic extract (of at most 7% by weight, generally of at most 5% or of at most 2% by weight, excluding the extraction solvent) was thus reduced.

The lower the DMSO content, the more the stage of crystallization of the furan compound (or more particularly of the 5-HMF) contained in the extract will be carried out under favorable conditions. The yield (and possibly the purity) of crystallized furan compound (or more particularly of crystallized 5-HMF) is thus improved.

The Crystallization Stage d)

Advantageously, the purified organic extract obtained in stage c) undergoes a crystallization stage and a filtration stage. Crystals of furan compound (or more particularly of 5-HMF) and a filtrate rich in solvent are produced.

The crystallization can be carried out by all the methods known to a person skilled in the art, such as, for example, by lowering the temperature, increasing the concentration of compound to be crystallized, increasing the concentration of compound to be crystallized with lowering of the temperature, or indeed even by adding a third compound which is a poor solvent for the compound to be crystallized.

The conditions are those known to a person skilled in the art. In the case of 5-HMF, the temperature is less than or equal to 30° C. and generally between −100° C. and 0° C., preferably between −50° C. and 0° C. and more preferably still between −40° C. and −10° C. In the case of the other furan derivatives which can be produced in DMSO starting from 5-HMF, the melting point of which is greater than that of 5-HMF, the temperature is less than or equal to 150° C. and generally between −100° C. and 30° C., preferably between −50° C. and 30° C.

According to the invention, the filtrate rich in solvent is advantageously recycled in stage b) in order to carry out a new extraction of 5-HMF or other furan compounds.

The filtrate is preferably recycled, partially or completely (after a possible purge), to the liquid-liquid extraction stage b).

According to the methods known to a person skilled in the art, stage d) is carried out in one or more passes, the crystals are washed and dried.

Figure 1:
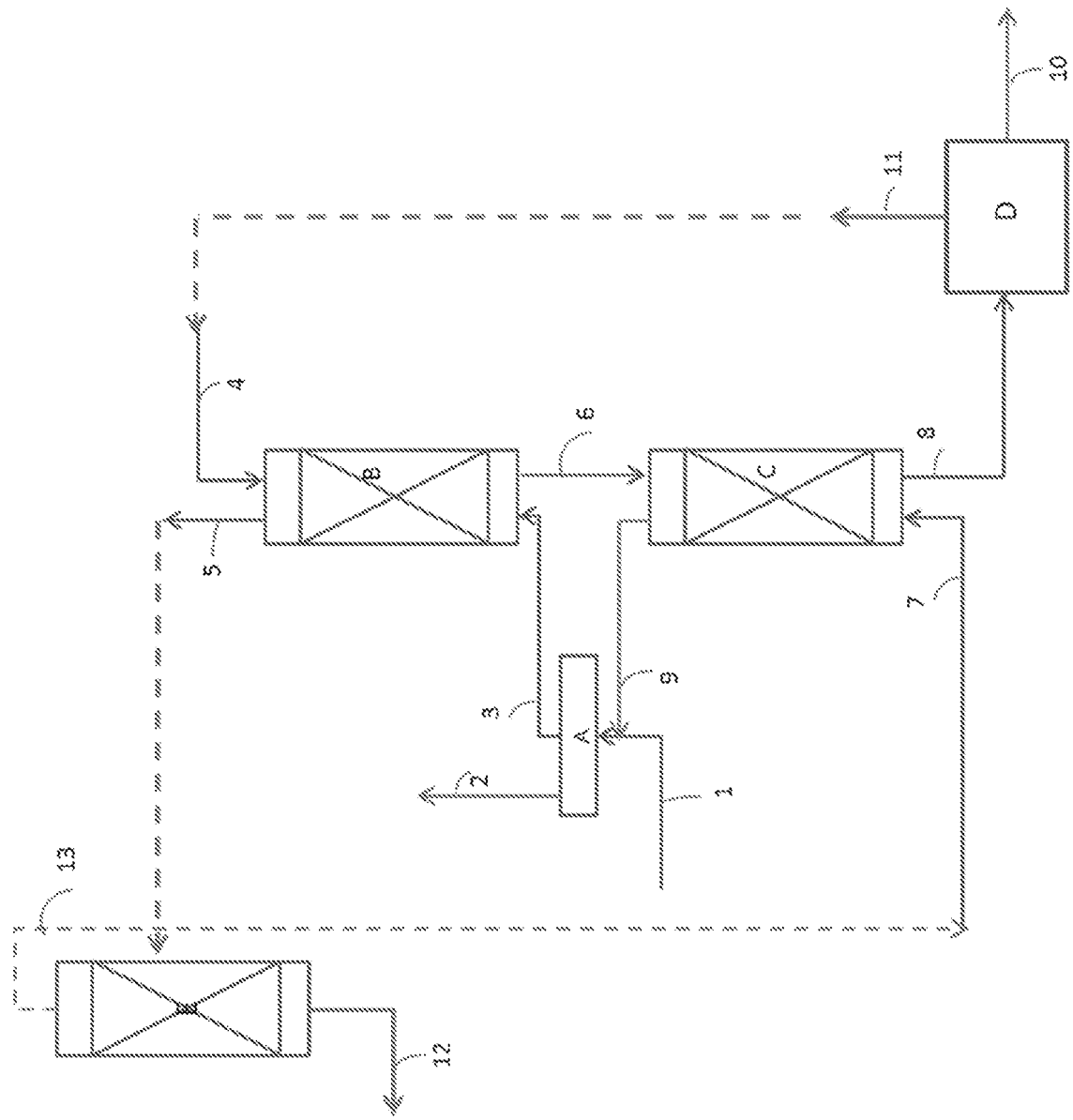
FIG. 1 illustrates an embodiment of the invention.

According to FIG. 1, which exhibits a preferred embodiment, the feedstock 1 containing at least 5-HMF or other furan compounds and DMSO is mixed according to stage a) in the mixing section A with the intermediate aqueous raffinate 9 resulting from the back-extraction stage c).

According to FIG. 1, the precipitated "humins" are filtered off in the filtration zone A and are discharged via the pipe 2. This zone may not exist or be bypassed, in particular in the case where the amount of humins in the feedstock is low.

The mixture obtained 3 (filtered or not) is sent to a liquid-liquid extractor B in order to carry out stage b) of extraction of the furan compound. The mixture 3 circulates countercurrentwise to the extraction solvent 4. On the one hand, an aqueous raffinate 5 depleted in furan compound and, on the other hand, an intermediate organic extract 6 enriched in furan compound are produced.

The intermediate organic extract 6 enriched in 5-HMF is directed to a second liquid-liquid extractor C in order to carry out stage c) of back-extraction with water. It circulates countercurrentwise to the backwashing water 7 added. On the one hand, an intermediate aqueous raffinate 9 enriched in DMSO and, on the other hand, a purified organic extract 8 are produced.

The purified organic extract 8 undergoes a crystallization stage d), for example by cooling, in a crystallizer D. The crystals of furan compounds in suspension in the solvent are subsequently recovered by filtration and dried. The furan compound is recovered in the solid form with a high purity (reference 10). The filtrate 11 rich in solvent is recycled as extraction solvent to the extractor B in order to carry out a new extraction stage b).

The aqueous raffinate 5 is subjected, for example, to a distillation in the distillation column E, so as to produce a residue rich in DMSO 12 and a distillate rich in water 13. The distillate rich in water 13 is recycled to the extractor C as water added in order to carry out a new back-extraction stage c).

Figure 2:
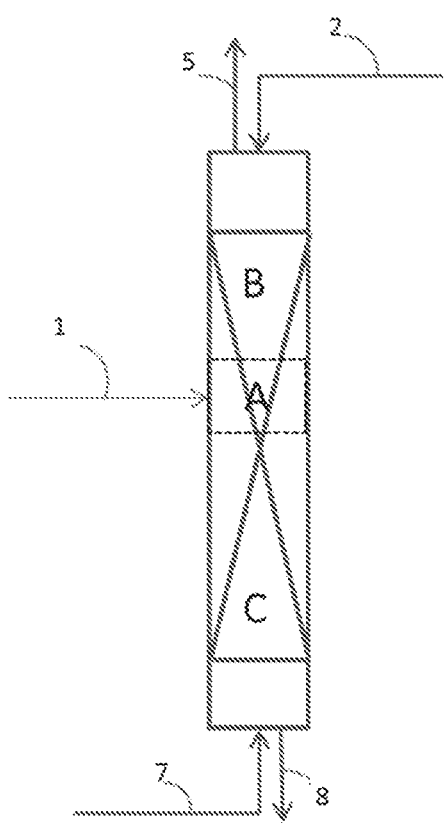
FIG. 2 illustrates a further embodiment of the invention.

The figures illustrate a preferred embodiment of the invention without limiting it. Thus, in an embodiment of the invention represented in FIG. 2, the extraction stage b) and the back-extraction stage c) can be carried out in one and the same unit operation, in particular when the concentration of humins is low (1% by weight or less). Thus, one and the same liquid-liquid extraction column is used to carry out stages b) and c). The feedstock 1 enters this column at an intermediate point located between the point of injection of the solvent and the point of injection of the backwashing water. This point of injection of the feedstock constitutes the zone A. Assuming that the extraction solvent is denser than water, the part higher than said point of injection of the feedstock constitutes the extraction zone B and the part lower than said point of injection constitutes the back-extraction zone C.

The extraction zone B operates according to stage b). The intermediate organic extract resulting from the extraction zone B (which corresponds to the reference 6 of FIG. 1) descends by gravity into the back-extraction zone C, passing here through the mixing zone A.

The back-extraction zone C operates according to stage c). The intermediate aqueous raffinate originating from the back-extraction zone C (which corresponds to the reference 9 of FIG. 1) rises by gravity into the extraction zone B, passing through the mixing zone A, where it is found in contact with the feedstock 1. The purified extract 8 which exits from the back-extraction zone C can advantageously undergo a crystallization stage d).

Thus, in the embodiment of FIG. 1, stages a), b) and c) are carried out in different separate zones. On the other hand, in the embodiment of FIG. 2, stages a), b) and c) are carried out in different non-separated zones; this embodiment is highly suitable when the amount of humins is 1% by weight or less (measured by size exclusion chromatography).

EXAMPLES

The examples below illustrate the invention without limiting the scope thereof.

Example 1: Process According to the Invention

In order to show the advantages of the presence of a back-extraction stage, the results of simulation of stage c) of the process according to the invention operated according to FIG. 1 are presented here.

The operating conditions are for stage a): a DMSO/5-HMF ratio by weight in the feedstock of 55/45, and there is no water in the feedstock. The feedstock flow rate is 100 kg/h. The flow rate of water originating from stage c) is the same in all the simulated cases.

The operating conditions of stage b): the solvent is pure dichloromethane (DCM) (no DMSO or 5-HMF). The solvent flow rate is 185 kg/h. The number of theoretical stages of the extraction section is constant and fixed at 4. The stage is operated at a temperature of 20° C.

The operating conditions of stage c): pure water is used, with a flow rate of 100 kg/h. The temperature is 20° C. The number of theoretical stages of the back-extraction section (referred to as NTS backwashing in table 1) are varied. The lower the number, the greater the trend toward the process described in the patent FR 2 669 635 (no back-extraction stage).

The simulation tool used establishes a material balance with regard to each constituent, stage by stage, while respecting a partitioning of the constituents between the two phases within each stage. This partitioning of the constituents was measured beforehand in the laboratory, for compositions characteristic of the extraction section (aqueous phase rich in DMSO and solvent phase poor in 5-HMF) and of the back-extraction section (aqueous phase poor in DMSO and solvent phase rich in 5-HMF).

TABLE 1

| NTS backwashing | 5-HMF extraction yield (%) | DMSO extraction yield (%) |
| --- | --- | --- |
| 1 | 99.1 | 8.7 |
| 2 | 99.0 | 2.6 |
| 3 | 99.0 | 0.8 |
| 4 | 99.0 | 0.2 |
| 5 | 99.0 | 0.1 |
| 6 | 99.0 | 0 |

The extraction yield is defined as the amount of 5-HMF (or respectively of DMSO) recovered in the extract produced in stage c), divided by the amount of 5-HMF (or respectively of DMSO) introduced in the feedstock.

The table above shows that the conditions of stage c) are adjusted as a function of the amount of DMSO acceptable in the extract sent for crystallization.

Example 2: Coupling of the Process According to the Invention Having NTS=1 and of the Process for Crystallization at −18° C.

In this example, the synergistic effect which exists between the liquid-liquid extraction process according to the invention and the crystallization process is illustrated.

The results of Example 1 are taken up, in the case where the number of theoretical stages NTS of backwashing is equal to 1. The extraction yield is 99.1% for 5-HMF and 8.7% for DMSO. In view of the composition of the feedstock, an extract is thus obtained composed (by weight) of 19% of 5-HMF, 2% of DMSO and 79% of DCM.

A first stage of evaporation of a part of the DCM solvent contained in the extract is then carried out, which makes it possible to concentrate the 5-HMF and the DMSO up to concentrations of 30% and 3% respectively (DMSO/5-HMF ratio by weight of 0.1).

This concentrated extract is subsequently cooled to a temperature of −18° C. The 5-HMF then crystallizes with a yield of 22%. The DMSO does not crystallize under these conditions and remains in solution.

After a filtration stage, a filtrate is thus recovered, the composition by weight of which is as follows: 72.6% of DCM, 3.1% of DMSO and 24.3% of 5-HMF.

Example 3: Coupling of the Process According to the Invention Having NTS=6 and of the Process for Crystallization at −18° C.

The results of Example 1 are taken up, in the case where the NTS of backwashing is equal to 6. The extraction yield is 99% for 5-HMF and 0% for DMSO. In view of the composition by weight of the feedstock, an extract is thus obtained composed (by weight) of 19% of 5-HMF and 81% of DCM.

A first stage of evaporation of a part of the DCM solvent contained in the extract is then carried out, which makes it possible to concentrate the 5-HMF up to a concentration of 30% (DMSO/5-HMF ratio by weight of 0).

This concentrated extract is subsequently cooled to a temperature of −18° C. The 5-HMF then crystallizes with a yield of 38.5% (cf. example 1).

After a filtration stage, a filtrate is thus recovered, the composition by weight of which is as follows: 79.1% of DCM and 20.9% of 5-HMF.

Example 4: Coupling of the Process According to the Invention Having NTS=6 and of the Process for Crystallization at −30° C.

The results of Example 1 are taken up, in the case where the NTS of backwashing is equal to 6. The extraction yield is 99% for 5-HMF and 0% for DMSO. In view of the composition by weight of the feedstock, an extract is thus obtained composed (by weight) of 19% of 5-HMF and 81% of DCM.

A first stage of evaporation of a part of the DCM solvent contained in the extract is then carried out, which makes it possible to concentrate the 5-HMF up to a concentration of 30% (DMSO/5-HMF ratio by weight of 0).

This concentrated extract is subsequently cooled to a temperature of −30° C. The 5-HMF then crystallizes with a yield of 84%.

After a filtration stage, a filtrate is thus recovered, the composition of which is as follows: 95.3% of DCM and 4.7% of 5-HMF.

In conclusion, these various cases studied show the advantage of the process according to the invention comprising a back-extraction stage which makes it possible to produce an extract containing 5-HMF but containing little or no DMSO, which facilitates the crystallization of the 5-HMF.

Example 5: Comparison with the Prior Art FR-2 669 635 as Regards the Crystallization of the 5-HMF The crystallization of two extracts is compared here:
1) one containing 30% by weight of 5-HMF, 3% by weight of DMSO and 67% by weight of DCM, which is produced in the examples of the patent FR 2 669 635,
2) the other containing 30% by weight of 5-HMF and 70% by weight of DCM, which is produced by the present invention.

These two extracts are cooled to a temperature of −18° C. and the crystallization of the 5-HMF is observed (M.p.=approximately 30° C.). By lowering the temperature at constant composition, the concentration of the 5-HMF in the medium becomes greater than the solubility limit: the nucleation of 5-HMF crystals and their growth are then observed, until the concentration of 5-HMF is equal to the solubility limit at the temperature of −18° C. The time τ necessary to reach this equilibrium is noted, and the crystallization yield is then determined (amount of 5-HMF crystallized divided by the amount of 5-HMF initially present).

| Extract | 1) DMSO/5-HMF ratio by weight = 0.1 | 2) DMSO/5-HMF ratio by weight = 0 |
|---|---|---|
| Crystallization yield of the 5-HMF | 22% | 38.5% |
| τ (day) | 2 | <1 |

According to the examples provided in the patent FR 2 669 635, the ratio by weight of DMSO to 5-HMF in the extracts is typically of the order of 0.1. This ratio, of course, depends on many factors, such as the ratio by weight of DMSO to 5-HMF in the feedstock, the amount of water added to the feedstock (modifying the partition coefficients and thus the extraction selectivity), or indeed even the solvent flow rate (i.e. extraction yield). Nevertheless, the DMSO/5-HMF ratio by weight cannot be reduced to zero in the invention described in the patent FR 2 669 635.

When it is desired to crystallize an extract in which the ratio by weight of DMSO/5-HMF is 0.1, as in the examples provided in the patent FR 2 669 635, it is found that the nucleation and the growth of the crystals are slow. In addition, at a temperature of −18° C., the thermodynamically achievable crystallization yield is only 22%.

When the same experiment is carried out with an extract no longer containing DMSO but only 5-HMF, a nucleation and growth of the crystals is observed which is at least twice as fast, and the thermodynamically achievable crystallization yield is markedly increased, changing from 22% in the presence of DMSO to 38.5% in the absence of DMSO.

The advantage of producing an extract not containing DMSO but only 5-HMF, so as to reduce the operating and capital costs associated with the stage of crystallization of the 5-HMF, is clearly understood here.

The invention claimed is:
1. A process for the separation of furan compound(s) contained in a feedstock also comprising dimethoxysulfoxide, said process successively comprising:
   a) bringing said feedstock into contact with an intermediate aqueous raffinate enriched in dimethoxysulfoxide and optionally filtering the resultant mixture,
   b) subjecting said mixture to extraction by an organic solvent, wherein said solvent is a chlorinated solvent, an ether, a ketone or an aromatic compound, to produce an aqueous raffinate enriched in dimethoxysulfoxide and an intermediate organic extract enriched in furan compound(s), c) subjecting said intermediate organic extract enriched in furan compound(s) to back-extraction to produce said intermediate aqueous raffinate enriched in dimethoxysulfoxide and a purified organic extract, and said intermediate aqueous raffinate is introduced, partially or completely, into contact with said feedstock, and d) crystallizing the furan compound, followed by filtration, to obtain the crystallized furan compound and solvent.

2. The process as claimed in claim 1, wherein the furan compound is 5 hydroxymethylfurfural, 2,5-diformylfuran, 2,5-furandicarboxylic acid, dimethyl 2,5-furandicarboxylate (DMFDCA), or any mixture thereof.

3. The process as claimed in claim 1, wherein the furan compound is 5-hydroxymethylfurfural.

4. The process as claimed in claim 1, wherein the aqueous raffinate enriched in dimethoxysulfoxide produced in stage b) is distilled to obtain a residue rich in dimethoxysulfoxide and a distillate rich in water.

5. The process as claimed in claim 4, wherein the distillate rich in water is recycled, partially or completely, for use in said back-extraction in c).

6. The process as claimed in claim 1, wherein the solvent used in b) is a $C_1$-$C_{10}$ chlorinated solvent, a $C_2$-$C_{10}$ ether, a $C_2$-$C_{10}$ ketone, or a $C_4$-$C_{10}$ aromatic compound.

7. The process as claimed in claim 1, wherein the solvent used in b) is dichloromethane, diethyl ether, diisopropyl ether, methyl ethyl ketone, methyl isopropyl ketone, thiophene, anisole, or toluene.

8. The process as claimed in claim 1, wherein b) and c) are each performed countercurrently at a temperature of between 0° C. and 60° C.

9. The process as claimed in claim 1, wherein back-extraction water introduced in c) contains less than 1% by weight of dimethoxysulfoxide.

10. The process as claimed in claim 1, wherein the filtrate resulting from d) is recycled, partially or completely, to b).

11. The process as claimed in claim 1, wherein the amount of water in said mixture is from 10% to 90% by weight.

12. The process as claimed in claim 1, wherein, in c), said intermediate aqueous raffinate contains at least 60% by weight of water.

13. The process as claimed in claim 1, wherein b) and c) are carried out in different separate zones.

14. The process as claimed in claim 1, wherein said feedstock contains 1% by weight or less of humins, and b) and c) are carried out in different non-separated zones.

15. The process as claimed in claim 1, wherein the solvent used in b) is dichloromethane.

16. The process as claimed in claim 1, wherein b) and c) are each performed countercurrently at a temperature of between 10° C. and 30° C.

17. The process as claimed in claim 5, wherein back-extraction water introduced in c) contains less than 1% by weight of dimethoxysulfoxide.

18. The process as claimed in claim 5, wherein a) includes filtering the resultant mixture.

19. The process as claimed in claim 17, wherein a) does not include filtering the resultant mixture.

* * * * *